United States Patent [19]

Shum

[11] Patent Number: 4,946,812

[45] Date of Patent: Aug. 7, 1990

[54] CATALYST FOR UPGRADING LIGHT PARAFFINS

[75] Inventor: Victor K. Shum, Naperville, Ill.

[73] Assignee: Amoco Corporation, Chicago, Ill.

[21] Appl. No.: 256,414

[22] Filed: Oct. 12, 1988

Related U.S. Application Data

[62] Division of Ser. No. 82,031, Aug. 15, 1987, Pat. No. 4,808,763.

[51] Int. Cl.$^5$ .............................................. B01J 29/04
[52] U.S. Cl. .................................... 502/61; 502/66; 502/71
[58] Field of Search .................... 502/61, 66, 71, 74

[56] References Cited

U.S. PATENT DOCUMENTS

| | | | |
|---|---|---|---|
| 3,259,564 | 7/1966 | Kimberlin, Jr. ....................... | 502/66 |
| 3,702,886 | 11/1972 | Argaller et al. ....................... | 502/61 |
| 4,079,092 | 3/1978 | Hayes et al. .......................... | 502/74 |
| 4,392,989 | 7/1983 | Chu et al. ............................. | 502/61 |
| 4,452,907 | 6/1984 | Ball et al. ............................. | 502/61 |
| 4,581,215 | 4/1986 | Kaeding ................................ | 502/71 |
| 4,585,641 | 4/1986 | Barri et al. ............................ | 502/61 |
| 4,615,997 | 10/1986 | Chem et al. ........................... | 502/74 |
| 4,627,912 | 12/1986 | Field ..................................... | 585/419 |
| 4,645,751 | 2/1987 | McCullen et al. .................... | 502/71 |
| 4,704,494 | 11/1987 | Inui ...................................... | 585/417 |

FOREIGN PATENT DOCUMENTS

| | | | |
|---|---|---|---|
| 3419280 | 1/1985 | Fed. Rep. of Germany ........ | 502/74 |
| WO84/03879 | 10/1984 | PCT Int'l Appl. ................. | 585/417 |

OTHER PUBLICATIONS

Csiesery, *Ind. Eng. Chem. Process Des. Dev.*, vol. 18, No. 2, 1979, pp. 191–197.

Bernard, *Proced. 5th Conf. on Zeolites* (1980), Heyden, London, pp. 686–695.

*Primary Examiner*—Carl F. Dees
*Attorney, Agent, or Firm*—Ekkehard Schoettle; William H. Magidson; Ralph C. Medhurst

[57] ABSTRACT

The present invention relates to a process for producing aromatic compounds from a hydrocarbon gas containing paraffinic hydrocarbons under conversion conditions in the presence of a catalyst comprising a gallosilicate molecular sieve and a platinum metal component.

6 Claims, No Drawings

4,946,812

CATALYST FOR UPGRADING LIGHT PARAFFINS

CROSS-REFERENCE TO RELATED APPLICATIONS

This is a division of application Ser. No. 082,031, filed on Aug. 5, 1987, now U.S. Pat. No. 4,808,763.

BACKGROUND OF THE INVENTION

The present invention is directed to a process for upgrading light paraffins such as ethane, propane, and butanes. Interest in upgrading these light paraffins has been growing due to recent and anticipated changes in refinery processing schemes which resulted and will result in a greater supply of such light paraffins. These changes include: the higher severity operation of the reforming process in order to maintain a high octane rating in the absence of or reduction of the lead content in gasoline; the lowering of reid vapor pressure (RVP) specifications; the increased use of oxygenates such as methyl tertiary butyl ether (MTBE) and ethanol resulting in the removal of butanes from the gasoline pool; the increased demand for jet fuel necessitating increased gas oil hydrocracking resulting in more light gas production, and the increase in operating temperatures in fluidized catalytic crackers resulting in more light gas production. Thus, there is great incentive to investigate means for converting these materials into more valuable liquids such as transportation fuels or chemical feedstocks.

The upgrading or conversion of light paraffinic gases and synthesis gas has previously been carried out in the presence of gallium-based or gallium-containing catalysts.

U.S. Pat. No. 4,543,347 (Heyward et al.) discloses a catalyst composition suitable for converting synthesis gas to hydrocarbons which is a mixture of zinc oxide and an oxide of at least one metal selected from gallium and iridium, an oxide of at least one additional metal collected from the elements of Group IB, II through V, VIB and VIII including the lanthanides and actinides and a porous crystalline tectometallic silicate.

U.S. Pat. No. 4,490,569 (Chu et al.) discloses a process for converting propane to aromatics over a zincgallium zeolite. This zeolite optionally may also contain palladium. More specifically, the catalyst composition used in the instant patent consists essentially of an aluminosilicate having gallium and zinc deposited thereon or an aluminosilicate in which cations have been exchanged with gallium and zinc ions wherein the aluminosilicate is selected from the group known as ZSM-5 type zeolites.

U.S. Pat. No. 4,585,641 (Barri et al.) discloses crystalline gallosilicates which may be impregnated, ion exchanged, admixed, supported or bound for catalyzing a reaction such as alkylation, dealkylation, dehydrocyclodimerization, transalkylation, isomerization, dehydrogenation, hydrogenation, cracking, hydrocracking, cyclization, polymerization, conversion of carbon monoxide and hydrogen mixtures through hydrocarbons and dehydration reaction. The metal compounds which may be used for ion exchange or impregnation may be compounds of any one of the groups of metals belonging to Groups IB, IIB, IIIA, IVA, VA, VIB, VIIB and VIII according to the Periodic Table. Specifically, preferred compounds include copper, silver, zinc, aluminum, gallium, indium, vanadium, lead, antimony, bismuth, chromium, molybdenum, tungsten, manganese, iron, cobalt, nickel, ruthenium, rhodium, palladium, iridium, platinum, radium, thorium and the rare earth metals. Patentees describe their gallosilicate as "Gallo Theta-1" in contradistinction to an MFI-type gallosilicate which has a substantially different X-ray diffraction pattern.

U.S. Pat. No. 4,350,835 (Chester et al.) relates to a catalytic process for converting gaseous feedstocks containing ethane to liquid aromatics by contacting the feed in the absence of air or oxygen under conversion conditions with a crystalline zeolite catalyst having incorporated therein a minor amount of gallium thereby converting the ethane to aromatics. The gallium is present in the catalyst as gallium oxide or as gallium ions if cations in the aluminosilicate have been exchanged with gallium ions. The patent further discloses that the original alkali metal of the zeolite, when it has been synthesized in the alkali metal form, may be converted to the hydrogen form or be replaced by ion exchange with other suitable metal cations of Groups I through VIII of the Periodic Table, including nickel, copper, zinc, palladium, calcium or rare earth metals.

European Patent Application 0 107 876 discloses a process for producing an aromatic hydrocarbon mixture from a feedstock containing more than 50 wt.% $C_2$ through $C_4$ paraffins. Specifically the process is carried out in the presence of crystalline gallium-silicate having a $SiO_2/Ga_2O_3$ molar ratio of 25 to 250 and a $Y_2O_3/GaO_3$ molar ratio lower than 1 where Y can be aluminum, iron, cobalt or chromium. The disclosure also teaches a two-step silicate treatment comprising a coke deposition and a coke burn-off with an oxygen-containing gas.

European Patent Application 0 107 875 similarly discloses a process for producing an aromatic hydrocarbon mixture from a feedstock comprising more than 50 wt.% of $C_2$ through $C_4$ paraffins. This process is carried out in the presence of a crystalline gallium-silicate, having a $SiO_2/Ga_2O_3$ molar ratio of 25 to 100 and a $Y_2O_2/Ga_2O_3$ molar ratio lower than 1 where Y can be aluminum, iron, cobalt or chromium.

Light paraffinic gases have also been upgraded to liquid aromatics in the presence of crystalline aluminosilicate zeolite catalysts having incorporated therein a minor amount of a metal selected from Groups VIII, IIB, and IB of the Periodic Table. For instance, U.S. Pat. No. 4,120,910 (Chu) discloses copper-zinc-HZSM-5, platinum-HZSM-5, copper-HZSM-5, and zinc-HZSM-5 catalysts suitable for upgrading a gaseous paraffinic hydrocarbon feed to aromatic compounds.

It has now been discovered that $C_2$ through $C_5$ light paraffins can most effectively be upgraded by the catalytic process of the present invention minimizing methane and ethane production while simultaneously minimizing the production of undesirable heavy aromatics such as naphthalenes.

SUMMARY OF THE INVENTION

Briefly stated, in a broad aspect, this invention relates to a process for producing aromatic compounds from a hydrocarbon gas containing paraffinic hydrocarbons under conversion conditions in the presence of a catalyst comprising a gallosilicate molecular sieve and a platinum metal component.

DETAILED DESCRIPTION OF THE INVENTION

The present invention deals with the conversion to aromatic compounds of a hydrocarbon gas containing paraffinic hydrocarbons. A particularly suitable feedstock for use in the present invention contains $C_2$ through $C_5$ light paraffins or any fraction thereof in an amount where the gas contains at least 50 wt.% of such paraffins. A preferred feedstock is one which has a high propane content, typically, a liquefied petroleum gas (LPG). In addition to the mentioned paraffins, the feedstock may contain other light gases such as methane, ethane, propane, butene, isobutane, butadiene, and paraffins and olefins with five or more carbon atoms per molecule. These feedstocks are generally available from several sources in a refinery as elucidated above.

The process of the invention provides for the direct conversion of the light paraffinic gases to valuable aromatic hydrocarbons such as benzene, toluene, and xylenes. These aromatics can be used as an additive component to increase the octane number of gasoline or as raw materials in the petrochemical industry.

The process of the invention selectively provides for a high yield of benzene, toluene, and xylenes in the $C_{4+}$ product fraction while minimizing the yield of light $C_1$ through $C_2$ gases and $C_{9+}$ aromatic compounds in the product fraction.

Broadly, the catalyst employed according to the process of the present invention comprises a gallosilicate molecular sieve component and a platinum metal component. The gallosilicate can be prepared using conventional methods known to those skilled in the art. A suitable method is disclosed in European Patent Application 01 107 875 which is incorporated herein by reference.

In another method the gallosilicate crystalline molecular sieves of this invention are characterized by the representative X-ray pattern listed in Table 1 below and by the composition formula:

$$0.9 \pm 0.2\ M_{2/n}\ O:\ Ga_2O_3:ySiO_2:zH_2O$$

wherein M is at least one cation, n is the valence of the cation, y is between 4 and about 600, and z is between 0 and about 160. It is believed that the small gallium content of the sieves is at least in part incorporated in the crystalline lattice. Various attempts to remove the gallium from the gallosilicate sieves by exhaustive exchange with sodium, ammonium, and hydrogen ions were unsuccessful and therefore, the gallium content is considered nonexchangeable in the instant sieves prepared according to the present method.

TABLE 1

| d-Spacing Å (1) | Assigned Strength (2) | d-Spacing Å (1) | Assigned Strength (2) |
|---|---|---|---|
| 11.10 ± 0.20 | VS | 3.84 ± 0.10 | MS |
| 9.96 ± 0.20 | MS | 3.71 ± 0.10 | M |
| 6.34 ± 0.20 | W | 3.64 ± 0.10 | W |
| 5.97 ± 0.20 | W | 2.98 ± 0.10 | VW |
| 5.55 ± 0.20 | W | | |
| 4.25 ± 0.10 | VW | | |

(1) Copper K alpha radiation
(2) VW = very weak; W = weak; M = medium; MS = medium strong; VS = very strong A gallosilicate molecular sieve useful in this invention can be prepared by crystallizing an aqueous mixture, at a controlled pH, of a base, a gallium ion-affording material, an oxide of silicon, and an organic template compound.

Typically, the molar ratios of the various reactants can be varied to produce the crystalline gallosilicates of this invention. Specifically, the molar ratios of the initial reactant concentrations are indicated below:

TABLE 2

| | Broad | Preferred | Most Preferred |
|---|---|---|---|
| $SiO_2/Ga_2O_3$ | 4–200 | 10–150 | 20–100 |
| Organic base/$SiO_2$ | 0.5–5 | 0.05–1 | 0.1–0.5 |
| $H_2O/SiO_2$ | 5–80 | 10–50 | 20–40 |
| Template/$SiO_2$ | 0–1 | 0.01–0.2 | 0.02–0.1 |

By regulation of the quantity of gallium (represented as $Ga_2O_3$) in the reaction mixture, it is possible to vary the $SiO_2/Ga_2O_3$ molar ratio in the final product. In general, it is desirable to have the gallium content of the gallosilicate sieve of this invention between about 0.1 and about 8 percent by weight of gallium. More preferably, the amount of gallium should be between about 0.2 and about 6 weight percent gallium and, most preferably, between about 0.3 and about 4 weight percent of gallium. Too much gallium in the reaction mixture appears to reduce the sieve crystallinity which reduces the catalytic usefulness of the sieve.

More specifically, a material useful in the present invention is prepared by mixing a base, a gallium ion-affording substance, an oxide of silicon, and an organic template compound in water (preferably distilled or deionized). The order of addition usually is not critical although a typical procedure is to dissolve the organic base and the gallium ion-affording substance in water and then add the template compound. Generally, the silicon oxide compound is added with mixing and the resulting slurry is transferred to a closed crystallization vessel for a suitable time. After crystallization, the resulting crystalline product can be filtered, washed with water, dried, and calcined.

During preparation, acidic conditions should be avoided. Advantageously, the pH of the reaction mixture falls within the range of about 9.0 to about 13.0; more preferably between about 10.0 and about 12.0 and most preferably between about 10.5 and 11.5.

Examples of oxides of silicon useful in this invention include silicic acid, sodium silicate, tetraalkyl silicates, and Ludox, a stabilized polymer of silicic acid manufactured by E. I. DuPont de Nemours & Co. Typically, the oxide of gallium source is a water-soluble gallium compound such as gallium nitrate or gallium acetate or another gallium compound, the anion of which is easily removed during sieve calcination prior to use. Water insoluble gallium compounds such as the oxide can be used as well.

Cations useful in the formation of the gallosilicate sieves include the sodium ion and the ammonium ion. The sieves also can be prepared directly in the hydrogen form with an organic base such as ethylenediamine.

The acidity of the gallosilicate sieves of this invention is high as measured by the Hammett $H_o$ function which lies in the neighborhood of about −3 to about −6.

Organic templates useful in preparing the crystalline gallosilicate include alkylammonium cations or precursors thereof such as tetraalkylammonium compounds, especially tetra-n-propylammonium compounds. A useful organic template is tetra-n-propylammonium bromide. Diamines, such as hexamethylenediamine, can be used.

The crystalline gallosilicate molecular sieve can be prepared by crystallizing a mixture of sources for an oxide of silicon, an oxide of gallium, an alkylammonium compound, and a base such as sodium hydroxide, ammonium hydroxide or ethylenediamine such that the initial reactant molar ratios of water to silica range from about 5 to about 80, preferably from about 10 to about 50 and most preferably from about 20 to about 40. In addition, preferable molar ratios for initial reactant silica to oxide of gallium range from about 4 to about 200, more preferably from about 10 to about 150 and most preferably from about 20 to about 100. The molar ratio of base to silicon oxide should be about above about 0.5, typically below about 5, preferably between about 0.05 and about 1.0 and most preferably between about 0.1 and about 0.5. The molar ratio of aklylammonium compound, such as tetra-n-propylammonium bromide, to silicon oxide can range from 0 to about 1 or above, typically above about 0.005, preferably about 0.01 to about 0.2, most preferably about 0.02 to about 0.1.

The resulting slurry is transferred to a closed crystallization vessel and reacted usually at a pressure at least the vapor pressure of water for a time sufficient to permit crystallization which usually is about 0.25 to about 25 days, typically is about one to about ten days and preferably is about one to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about three to about seven days. Samples of material can be removed during crystallization to check the degree of crystallization and determine the optimum crystallization time.

The crystalline material formed can be separated and recovered by well-known means such as filtration with aqueous washing. This material can be mildly dried for anywhere from a few hours to a few days at varying temperatures, typically about 50° to about 225° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, the mildly dried product is calcined at temperatures ranging from about 260° to about 850° C. and preferably from about 425° to about 600° C. Extreme calcination temperatures or prolonged crystallization times may prove detrimental to the crystal structure or may totally destroy it. Generally, there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 hours. The gallosilicate sieves thus made generally have a surface area greater than about 300 sq. meters per gram as measured by the BET procedure.

Although not required, it is preferred to employ the above-described gallosilicate molecular sieve combined, dispersed or otherwise intimately admixed in a matrix of at least one non-molecular sieve, porous refractory inorganic oxide matrix component, as the use of such a matrix component facilitates the provision of the ultimate catalyst in a shape or form well suited for process use. Useful matrix components include alumina, silica, silicaalumina, zirconia, titania, etc., and various combinations thereof. The matrix components also can contain various adjuvants such as phosphorus oxides, boron oxides, and/or halogens such as fluorine or chlorine. Usefully, the molecular sieve-matrix dispersion contains about 1 to 99 wt.% of a sieve component, preferably 40 to about 90 wt.% and most preferably 45 to 85 wt.% of a sieve component based upon the sieve-matrix dispersion weight.

Methods for dispersing molecular sieve materials within a matrix component are well-known to persons skilled in the art and applicable with respect to the gallosilicate molecular sieve materials employed according to the present invention. A method is to blend the molecular sieve component, preferably in finely-divided form, in a sol, hydrosol or hydrogel of an inorganic oxide, and then add a gelling medium such as ammonium hydroxide to the blend, with stirring, to produce a gel. The resulting gel can be dried, shaped if desired, and calcined. Drying preferably is conducted in air at a temperature of about 80° to about 350° F. (about 27° to about 177° C.) for a period of several seconds to several hours. Calcination preferably is conducted by heating in air at about 800° to about 1,200° F. (about 427° to about 649° C.) for a period of time ranging from about ½ to about 16 hours.

Another suitable method for preparing a dispersion of the molecular sieve component in a porous refractory oxide matrix component is to dry blend particles of each, preferably in finely-divided form, and then shape the dispersion if desired.

Alternatively, in another method, the sieve and a suitable matrix material like alpha-alumina monohydrate such as Conoco Catapal SB Alumina can be slurried with a small amount of a dilute weak acid such as acetic acid, dried at a suitable temperature under about 200° C, preferably about 100° to about 150° C. and then calcined at between about 350° and about 700° C, more preferably between about 400° to about 650° C.

Silica-supported catalyst compositions can be made by dry mixing the gallosilicate sieve with a silica source such as Cab-O-Sil, adding water and stirring. The resulting solid is then dried below about 200° C. and finally calcined between about 350° C. and 700° C.

The platinum metal component of the catalyst employed according to the present invention can be present in elemental form, as oxides, as nitrates, as chlorides or other inorganic salts, or as combinations thereof. While other Group VIII metals can be employed in the present invention, platinum is preferred because it is relatively inactive for hydrogenolysis which would result in undesirable increased yields of $C_1$ and $C_2$.

Relative proportions of the sieve component and the platinum metal component are such that at least a catalytically-effective amount of each is present.

The platinum metal component content preferably ranges from about 0.01 to about 10 wt.%, calculated as a zero valent metal and being based on the total weight of the catalytic final composite, with about 0.01 to about 5 wt.% being more preferred, with a range of 0.05 to 1.0 wt.% being most preferred. Higher levels of platinum can be employed if desired, though the degree of improvement resulting therefrom typically is insufficient to justify the added cost of the metal.

The platinum metal component of the catalyst employed according to this invention can be associated with the sieve component by impregnation of the sieve component, or the sieve component can be dispersed in a porous refractory inorganic oxide matrix, with one or more solutions of compounds of the platinum metal component which compounds are convertible to oxides on calcination. It also is contemplated, however, to impregnate a porous refractory inorganic oxide matrix component with such solutions of the platinum metal component and then blend the sieve component with the resulting impregnation product. Accordingly, the present invention contemplates the use of catalysts in which the platinum metal component is deposed on the sieve component, on a sieve matrix component dispersion or on the matrix component of a sieve matrix component.

The mechanics of impregnating the sieve component, matrix component or matrix composite with solutions of compounds convertible to metal oxides on calcination are well-known to persons skilled in the art and generally involve forming solutions of appropriate compounds in suitable solvents, preferably water, and then contacting the sieve matrix component or sieve matrix dispersion with an amount or amounts of solution or solutions sufficient to deposit appropriate amounts of metal or metal salts onto the sieve or sieve matrix dispersion. Useful metal compounds convertible to oxides are well-known to persons skilled in the art and include various ammonium salts as well as metal acetates, nitrates, anhydrides, etc.

In another embodiment of the present invention the platinum metal component-gallosilicate containing catalyst also contains chloride. The addition of chloride to the catalyst serves to increase the conversion and selectivity of the process of the invention to aromatics. A convenient method of adding the chloride is to include a predetermined volume of a solution containing a predetermined concentration of hydrochloric acid in the impregnating solution used to incorporate the platinum metal component with the catalyst.

Alternatively, the chloride can also be added during the impregnation of the metal salt if the metal salt contains chloride, such as hydrogen hexachloroplatinate ($H_2PtCl_6 \cdot 6H_2O$) If the chloride content in the chloride-containing metal salt is not sufficiently high, additional chloride can be added by the addition of hydrochloric acid to the impregnating solution.

In the instant embodiment of the invention the catalyst broadly contains 0.1 to 10 wt.% chloride, preferably 0.5 to 5 wt.% chloride and most preferably 0.5 to 1.5 wt.% chloride based on the final catalyst weight.

Also contemplated within the purview of the present invention chloride can be incorporated into the catalyst by the addition of chloride-containing compounds to the feed stream such as carbon tetrachloride, hydrochloric acid, in amounts such that the final catalyst contains the above prescribed amount of chloride.

The above-described catalysts can be employed in any suitable form such as spheres, extrudates, pellets, or C-shaped or cloverleaf-shaped particles.

The process of the present invention is carried out under suitable operating conditions set out below in Table 3 under which the feed is contacted with the abovedescribed catalyst. It is also contemplated that a portion of the unconverted effluent stream can be recycled to the feed after separation from the aromatic products.

TABLE 3

|  | Broad | Preferred | Most Preferred |
|---|---|---|---|
| Conditions |  |  |  |
| Temperature, °F. | 700–1400 | 800–1200 | 850–1150 |
| Total Pressure, psig | 0–500 | 0–300 | 0–100 |
| WHSV, $h^{-1}$ | 0.1–100 | 0.1–40 | 0.1–20 |

The present invention is described in further detail in connection with the following examples, it being understood that the same are for purposes of illustration only and not limitation.

EXAMPLE 1

The present example demonstrates the process in accordance with the present invention.

A gallosilicate molecular sieve was prepared in a conventional manner using tetrapropylammonium bromide as the template compound and gallium oxide as the source of gallium. The gallium to silicon molar ratio of the finally prepared gallosilicate sieve was determined to be 0.069. The subject molecular sieve possessed an MFI or pentasil structure.

The so-prepared gallosilicate molecular sieve was subsequently dispersed in Catalpal B alumina (alpha alumina monohydrate) in amounts to achieve a ratio of 45 wt.% sieve to 55 wt.% alumina. Specifically, the gallosilicate sieve powder and alumina powder were mechanically mixed, then blended with 5 % acetic acid to form a gel. This gel was dried at 130° C. overnight and calcined in flowing air at 600° C. overnight.

The gallosilicate-alumina composition was then impregnated with an aqueous solution of tetraamine platinum (II) nitrate using the method of incipient wetness impregnation. This impregnation resulted in a composition having a 0.1 wt.% platinum content. This platinum impregnated gallosilicate-alumina composition was then dried at 70° C. overnight followed by a calcination in flowing air at 1000° F. (538° C) for 1 hour. The catalyst was then activated by drying it in flowing nitrogen at 1000° F. for a half-hour followed by a reduction step with hydrogen at 1000° F. for 1 hour.

The catalyst was then tested for propane conversion in a continuous flow fixed bed downflow reactor under the following conditions as set out in Table 4 below:

TABLE 4

| Temperature | 1000° F. |
|---|---|
| Pressure | 50 psig |
| Catalyst weight | 1.5 g |
| Propane liquid rate | 24 ml/h |
| Nitrogen diluent rate | 100 cc (NTP) per minute |

The above test resulted in a total conversion of 29.5 wt.%. Conversion is defined as the weight of all products in the effluent other than the feed components, in this case propane, as a percentage of the weight of the feed components. The product distribution in wt.% is set out below in Table 5.

TABLE 5

| Methane | 1.9 |
|---|---|
| Ethane | 27.3 |
| $C_4$ through $C_8$ aliphatics | 16.9 |

TABLE 5-continued

| | |
|---|---|
| Benzene | 13.0 |
| Toluene | 22.2 |
| Ethylbenzene | 1.0 |
| Para and metaxylenes | 7.5 |
| Orthoxylene | 1.5 |
| $C_9+$ material | 2.2 |
| Hydrogen | 6.5 |

The above product distribution shows the superior selectivity of the process of the invention. This is exemplified by the low $C_1$ and $C_2$ light gas production, high hydrogen production, high concentrations of benzene, toluene and xylenes in the $C_4+$ product fraction and the low $C_9+$ material production.

EXAMPLE 2

The present comparative example serves to show the superiority of the process of the invention over a prior art process that employs a zinc-ZSM-5 catalyst.

Specifically, a ZSM-5 zeolite was prepared by digesting a mixture of water, sodium aluminate, Ludox AS-40 and tetra-propyl-ammonium bromide in an autoclave under autogeneous pressure at 300° F. Appropriate amounts of Ludox AS-40 and sodium aluminate were used to provide a $SiO_2$ to $Al_2O_3$ molar ratio of 30. The crystallized product was subsequently filtered, washed repeatedly with distilled water and dried at 250° F. The so-dried material was then calcined at 1000° F. followed by an exchange with ammonium nitrate and a washing with distilled water.

The $NH_4$-ZSM-5 zeolite was then exchanged with excess zinc nitrate three times followed by repeated washings with distilled water. The zinc-exchanged ZSM-5 zeolite was then filtered and dried at 250° F. The final catalyst had a zinc content of 1.02 wt.%. The Zn-ZSM-5 zeolite was then wet-mulled and extruded with Catapal alumina to yield a 1/16-inch extrudate containing 80 wt.% zeolite and 20 wt..% alumina. The extrusion step was followed by a drying step at 250° F. and a calcination step at 1000° F.

The platinum-gallosilicate catalyst used in the present example was prepared substantially in the same manner as the platinum-gallosilicate prepared in Example 1. In this case, the catalyst contained gallium to silicon ratio of 0.035.

The following Table 6 sets out results of a comparison pilot plant test of the Pt/Ga-silicate of the invention and the prior art Zn-ZSM-5 at the same level of conversion.

TABLE 6

Comparison of Zn-ZSM-5 and Pt/Ga-Silicate

| Catalyst | Zn-ZSM-5 (20% binder) | Pt/Ga-silicate (45% binder) |
|---|---|---|
| Feed | 100% $C_3H_8$ | 100% $C_3H_8$ |
| WHSV, g propane/g cat. h | 9.4 | 9.4 |
| Temperature, °F. | 930 | 1000 |
| Reactor pressure, psig | 50 | 50 |
| Conversion per pass, % w/w | 29 | 29 |
| Hydrocarbon Distribution, % w/w | | |
| C1 | 19 | 3 |
| C2 | 22a | 24b |
| $C_{4+}$ aliphatics | 21 | 24 |
| B | 7 | 9 |
| T | 17 | 25 |
| X | 10 | 12 |
| $C_{9+}$ | 4 | 3 |
| $C_{1,2}$ total | 41 | 27 |
| BTX total | 34 | 46 |

$^a C_2H_4/(C_2H_4 + C_2H_6) = 0.09$ mole fraction ethene
$^b C_2H_4/(C_2H_4 + C_2H_6) = 0.01$ mole fraction ethene The above Table clearly shows that the process of the invention possesses greater selectivity towards desirable BTX production, about 35% greater, than the prior art process employing the Zn-ZSM-5 catalyst, and a lower selectivity towards $C_1$ and $C_2$ production, about 34% lower than the Zn-ZSM-5 process.

EXAMPLE 3

The present example is provided to show the stability of the catalyst employed in the process of the invention.

A catalyst prepared in substantially the same manner as the one described in Example 1 was employed in the present example. This catalyst contained a gallium to silicon molar ratio of 0.035.

Table 7 below shows the operating conditions employed and the results achieved when the process of the invention was carried out for an extended period of time using the above-described catalyst.

TABLE 7

Propane Aromatization on Pt/Ga-Silicate

| Catalyst | Pt/Ga-Silicate (60 wt. % Sieve) | | | | | | | |
|---|---|---|---|---|---|---|---|---|
| Temperature, °F. | 1000° | | | | | | | |
| Reactor pressure, psig | 50 | | | | | | | |
| Feed | 100% $C_3H_8$ | | | | | | | |
| WHSV, g propane/g cat. h | 9.4 | | | | | | | |
| Time-on-stream, hour | 1 | 2 | 3 | 4 | 5 | 6 | 7 | 8 |
| Conversion per pass, wt. % | 38.2 | 34.2 | 35.1 | 34.1 | 37.5 | 37.3 | 36.5 | 36.0 |
| Hydrocarbon distribution, wt. % | | | | | | | | |
| Methane | 3.0 | 2.3 | 2.4 | 2.3 | 2.8 | 2.4 | 2.5 | 2.4 |
| Ethane | 25.5 | 23.5 | 24.6 | 24.7 | 26.5 | 25.0 | 25.9 | 25.7 |
| $C_{4+}$ aliphatics | 22.2 | 27.8 | 26.8 | 28.0 | 24.8 | 25.8 | 27.9 | 28.3 |
| Benzene | 9.8 | 8.0 | 7.9 | 7.5 | 9.3 | 8.5 | 7.8 | 7.7 |
| Toluene | 24.8 | 23.2 | 23.3 | 22.7 | 23.6 | 23.9 | 22.1 | 22.2 |
| Xylenes (incl. ethylbenzene) | 12.7 | 13.0 | 13.0 | 12.8 | 11.2 | 12.5 | 11.9 | 12.5 |
| $C_9+$ aromatics | 2.0 | 2.3 | 2.0 | 2.0 | 1.8 | 1.9 | 1.9 | 1.2 |
| Selectivity to Aromatics | 49.3 | 46.5 | 46.2 | 45.0 | 45.9 | 46.8 | 43.7 | 43.6 |
| Yield of Aromatics | 18.8 | 15.9 | 16.2 | 15.3 | 17.2 | 17.5 | 16.0 | 15.7 |

The above table clearly shows that the catalyst of the invention possess stability or a relatively slow deactivation rate with respect to aromatics production. Also, the conversion per pass remained relatively constant.

EXAMPLE 4

The present example serves to show that the use of a gallosilicate sieve in the absence of a platinum metal component not in accordance with the present invention results in a process possessing poor selectivity and conversion levels with respect to the desired aromatic products.

Specifically, a gallosilicate was prepared substantially as described in Example 1 except that the final gallium to silicon molar ratio was 0.035. The gallosilicate was subsequently pressed into pill form, which pills were subsequently comminuted and sieved to obtain 10-45 mesh size particles.

The following Table 8 sets out the conditions and results used and obtained in the present example when this catalyst was used to produce aromatics.

TABLE 8

| Catalyst | Ga-silicate (100% molec. sieve) | | |
|---|---|---|---|
| Temperature, °F. | 930 | | |
| Reactor pressure, psig | 50 | | |
| Feed | 100% $C_3H_8$ | | |
| WHSV, g propane/g cat. h | 9.4 | | |
| Time-on-stream, h | 1 | 2 | 3 |
| Conversion per pass, wt. % | 1.8 | 2.2 | 2.0 |
| Hydrocarbon Distribution, wt. % | | | |
| $C_1$ | 17.7 | 18.4 | 18.2 |
| $C_2$ | 41.8 | 41.1 | 42.0 |
| $C_{4+}$ aliphatics | 33.4 | 31.3 | 32.0 |
| Benzene | 1.2 | 1.5 | 1.3 |
| Toluene | 3.1 | 4.0 | 3.4 |
| Xylenes (incl. ethylbenzene) | 2.5 | 3.3 | 2.8 |
| $C_{9+}$ aromatics | 0.3 | 0.4 | 0.3 |

The above table clearly shows poor conversion and poor selectivity to aromatics in the absence of a platinum metal component in the catalyst.

EXAMPLE 5

The present example when considered in conjunction with the results of Example 3 serves to show that as the gallosilicate molecular sieve content of the sieve-alumina matrix is increased while keeping the platinum loading of the catalyst constant, the conversion increases markedly while the selectivity to aromatics increases less significantly when the process of the invention is carried out.

The following Tables 9 and 10 set out the conditions employed and results achieved for runs employing 13 wt.% sieve and 45 wt.% sieve respectively in the sieve-alumina matrix.

Each catalyst was prepared substantially as described in Example 1 except for the sieve contents. Each catalyst contained 0.1 wt.% Pt based on the final catalyst weight and each catalyst contained a gallosilicate having a gallium to silicon molar ratio of 0.035.

TABLE 9

| Catalyst | Pt/Ga-silicate (13% sieve) | | |
|---|---|---|---|
| Temperature, °F. | 1000 | | |
| Reactor pressure, psig | 50 | | |
| Feed | 100% $C_3H_8$ | | |
| WHSV, g propane/g cat. h | 9.4 | | |
| Time-on-stream, h | 1 | 2 | 3 |
| Conversion, wt. % | 11.5 | 11.0 | 10.5 |
| Hydrocarbon Distribution, wt. % | | | |
| $C_1$ | 2.2 | 2.5 | 2.7 |
| $C_2$ | 19.9 | 20.3 | 20.6 |
| $C_{4+}$ aliphatics | 39.3 | 39.6 | 39.9 |
| Benzene | 5.2 | 5.3 | 5.3 |
| Toluene | 18.3 | 18.2 | 17.7 |
| Xylenes (incl. ethylbenzene) | 11.5 | 11.0 | 10.7 |
| $C_{9+}$ aromatics | 3.6 | 3.2 | 3.1 |
| Selectivity to Aromatics, wt. % | 38.6 | 37.7 | 36.8 |
| Yield of Aromatics, wt. % | 4.4 | 4.1 | 3.9 |

TABLE 10

| Catalyst | Pt/Ga-silicate (45% sieve) | | | |
|---|---|---|---|---|
| Temperature, °F. | 1000 | | | |
| Reactor pressure, psig | 50 | | | |
| Feed | 100% $C_3H_8$ | | | |
| WHSV, g propane/g cat. h | 9.4 | | | |
| Time-on-stream, h | 1 | 2 | 3 | 4 |
| Conversion, wt. % | 28.0 | 30.2 | 30.7 | 30.0 |
| Hydrocarbon Distribution, wt. % | | | | |
| $C_1$ | 2.6 | 2.9 | 3.0 | 2.9 |
| $C_2$ | 23.5 | 25.4 | 26.2 | 26.1 |
| $C_{4+}$ aliphatics | 24.4 | 22.5 | 22.2 | 23.8 |
| Benzene | 9.2 | 9.3 | 9.2 | 8.8 |
| Toluene | 25.3 | 25.6 | 25.5 | 25.1 |
| Xylenes (incl. ethylbenzene) | 12.4 | 12.0 | 11.7 | 11.5 |
| $C_{9+}$ aromatics | 2.6 | 2.3 | 2.2 | 2.0 |
| Selectivity to Aromatics wt. % | 49.5 | 49.2 | 48.6 | 47.4 |
| Yield of Aromatics, wt. % | 13.9 | 14.9 | 14.9 | 14.2 |

When the results of the above Tables 9 and 10 are compared with Table 7 it is clear that increasing the sieve content increases conversion and aromatics selectivity.

EXAMPLE 6

The present example serves to show that the addition of chloride to the catalyst in accordance with the invention results in enhanced conversion and selectivity to aromatics.

In the present example a gallosilicate MFI zeolite having a gallium to silicon molar ratio of 0.035 was drymixed with Catalpal alumina (alpha-alumina monohydrate) to obtain 60 wt.% sieve-40 wt.% alumina matrix. Five percent acetic acid was then added to the powder till a paste was formed. During the addition of acetic acid, the wetted powder was continually stirred. The paste was dried overnight in a vacuum oven at 70° C. followed by calcination in a muffle furnace under air flow at 1100° F. for 18 hours. The gallosilicate-alumina matrix was then comminuted and sieved to obtain 10 to 45 mesh size particles. The platinum and chloride were added to the gallosilicate-alumina by incipient wetness impregnation. A predetermined amount of tetraamine platinum (II) nitrate and a predetermined amount of a 1M hydrochloric acid solution and distilled water were added together to yield the impregnating solution. After impregnation, the catalyst particles were dried at 70° C. in a vacuum oven overnight followed by calcination in a muffle furnace under air flow at 1000° F. for two hours. Enough tetraamine platinum (II) nitrate and hydrochloric acid were added to give 0.1 wt.% Pt and 1.0 wt.% Cl.

The following Table 11 sets out the conditions employed and the results achieved in the present example carried out in accordance with the present invention.

TABLE 11

| Catalyst | Pt/Ga-silicate/Cl (0.1 wt. % Pt, 1.0 wt. % Cl, 60% sieve) | | | |
|---|---|---|---|---|
| Temperature, °F. | 1000 | | | |
| Reactor pressure, psig | 50 | | | |
| Feed | 100% $C_3H_8$ | | | |
| WHSV, g propane/g cat. h | 9.4 | | | |
| Time-on-stream, h | 1 | 2 | 3 | 4 |
| Conversion, wt. % | 46.3 | 45.8 | 46.8 | 46.6 |
| Hydrocarbon Distribution, wt. % | | | | |
| $C_1$ | 5.0 | 5.2 | 5.2 | 5.5 |
| $C_2$ | 34.8 | 36.0 | 35.6 | 37.2 |
| $C_{4+}$ aliphatics | 11.4 | 11.6 | 11.3 | 11.1 |
| Benzene | 12.5 | 13.2 | 13.5 | 13.4 |
| Toluene | 23.1 | 22.1 | 22.5 | 21.6 |
| Xylenes (incl. ethylbenzene) | 10.1 | 9.2 | 9.2 | 8.7 |
| $C_{9+}$ aromatics | 3.1 | 2.7 | 2.7 | 2.5 |
| Selectivity to Aromatics, wt. % | 48.8 | 47.2 | 47.9 | 46.2 |

TABLE 11-continued

| Yield of Aromatics, wt. % | 22.6 | 21.6 | 22.4 | 22.5 |

The above table shows when compared with Table 7 (no chloride addition) that the addition of chloride increases the conversion and selectivity to aromatics. The $C_1$ and $C_2$ yields, however, are greater than in the case where chloride is not present.

What is claimed is:

1. A catalyst composition comprising a gallosilicate molecular sieve having the X-ray diffraction lines of Table 1 of the Specification, a platinum metal component, and a chloride component.

2. The composition of claim 1 wherein the platinum metal component is present in an amount ranging from about 0.01 to about 5 wt.% calculated as the zero valent metal and the chloride is present in an amount ranging from about 0.5 to 5 wt.% based on the total weight of the composition.

3. The composition of claim 1 wherein the platinum metal component is present in an amount ranging from about 0.05 to about 1.0 wt.% calculated as the zero valent metal and the chloride is present in an amount ranging from about 0.5 to about 1.5 wt.% based on the total weight of the composition.

4. The composition of claim 1 wherein said gallosilicate molecular sieve is dispersed within a nonmolecular sieve-containing porous refractory inorganic oxide matrix component.

5. The composition of claim 4 wherein said gallosilicate molecular sieve is present in the dispersion such that the weight of the gallosilicate ranges from about 45 to 85 wt.% based on the weight of the gallosilicate-refractory inorganic oxide dispersion.

6. The composition of claim 4 wherein the refractor inorganic oxide component is selected from the group consisting of silica, silica-alumina, and alumina.

* * * * *